(12) United States Patent
Mirhoseini et al.

(10) Patent No.: US 11,331,342 B2
(45) Date of Patent: May 17, 2022

(54) TREATMENT OF INFECTIONS AND ASSOCIATED PATHOPHYSIOLOGICAL CONDITIONS

(71) Applicants: Mahmood Mirhoseini, Germantown, WI (US); Aria Manasheri, Germantown, WI (US); Maryam Al Sadat Ahmadi, Germantown, WI (US); Siamak Nuhian, Germantown, WI (US)

(72) Inventors: Mahmood Mirhoseini, Germantown, WI (US); Aria Manasheri, Germantown, WI (US); Maryam Al Sadat Ahmadi, Germantown, WI (US); Siamak Nuhian, Germantown, WI (US)

(*) Notice: Subject to any disclaimer, the term of this patent is extended or adjusted under 35 U.S.C. 154(b) by 0 days.

(21) Appl. No.: 17/215,794

(22) Filed: Mar. 29, 2021

(65) Prior Publication Data

US 2021/0236762 A1 Aug. 5, 2021

Related U.S. Application Data

(60) Provisional application No. 63/001,438, filed on Mar. 29, 2020.

(51) Int. Cl.
  *A61K 33/00* (2006.01)
  *A61K 9/00* (2006.01)
  (Continued)

(52) U.S. Cl.
  CPC .............. *A61K 33/00* (2013.01); *A61K 9/007* (2013.01); *A61K 9/0019* (2013.01); *A61K 31/045* (2013.01); *A61K 31/7004* (2013.01); *A61M 15/02* (2013.01); *A61M 16/14* (2013.01); *A61N 5/062* (2013.01); *A61N 5/0624* (2013.01);
  (Continued)

(58) Field of Classification Search
  CPC ...... A61K 9/0019–0029; A61K 31/045; A61K 31/7004; A61K 41/0057; A61M 15/02; A61M 16/14–147; A61M 16/16–168; F24F 6/00–18
  See application file for complete search history.

(56) References Cited

U.S. PATENT DOCUMENTS

| 5,855,203 A * | 1/1999 | Matter | A61M 16/04 128/207.14 |
| 2006/0171956 A1* | 8/2006 | Bareholz | A61K 39/12 424/189.1 |

(Continued)

OTHER PUBLICATIONS

Caren, Linda D. et al.,"Effect of ethanol on the immune system in mice", Oct.-Nov. 1983, Science Direct, Toxicology Letters, vol. 19, Issues 1-2, pp. 147-153 (Year: 1983).*

(Continued)

*Primary Examiner* — Valerie L Woodward
(74) *Attorney, Agent, or Firm* — Barry Choobin; Patent 360

(57) ABSTRACT

Disclosed is a method of treating microbial infections and their associated complications in humans. The method includes administering to a patient, a composition of dextrose and ethanol. The composition can be administered in the form of an infusion. For patients suffering from respiratory complications, the disclosed method also provides for enhancing oxygen uptake by lungs and reducing oxygen resistance through the administration of air having helium gas and excited oxygen atoms.

6 Claims, 2 Drawing Sheets

(51) Int. Cl.
*A61K 31/045* (2006.01)
*A61K 31/7004* (2006.01)
*A61N 5/06* (2006.01)
*A61M 15/02* (2006.01)
*A61M 16/14* (2006.01)
*A61M 16/10* (2006.01)

(52) U.S. Cl.
CPC ..... *A61M 16/101* (2014.02); *A61M 2202/025* (2013.01); *A61M 2202/0208* (2013.01); *A61M 2202/0484* (2013.01); *A61M 2202/0486* (2013.01)

(56) References Cited

U.S. PATENT DOCUMENTS

| | | | |
|---|---|---|---|
| 2008/0078389 A1* | 4/2008 | Xiao | A61M 16/12 128/204.22 |
| 2013/0236358 A1* | 9/2013 | Latham | A61L 2/18 422/33 |
| 2018/0015052 A1* | 1/2018 | Radtke | A61K 31/4178 |
| 2018/0015310 A1* | 1/2018 | Choi | F24F 8/10 |
| 2018/0021531 A1* | 1/2018 | Stentiford | A61M 15/02 128/202.25 |

OTHER PUBLICATIONS

Pavia, Charles et al., "Influence of alcohol on antimicrobial immunity", Oct. 27, 2003, Elsevier, Biomedicine & Pharmacotherapy, pp. 84-89. (Year: 2003).*

Rutala, William A. et al., "Guideline for Disinfection and Sterilization in Healthcare Facilities, 2008", Updated May 2019, Centers for Disease Control and Prevention, pertinent pp. 39-40. (Year: 2019).*

* cited by examiner

TREATMENT OF INFECTIONS AND ASSOCIATED PATHOPHYSIOLOGICAL CONDITIONS

CROSS-REFERENCE TO RELATED APPLICATIONS

This application claims priority to the U.S. provisional patent application Ser. No. 63/001,438, filed on Mar. 29, 2020, which is incorporated herein by reference in its entirety.

FIELD OF INVENTION

The present disclosure relates to a method of treating an infection in humans, and more particularly, the present invention relates to a method of treating infections and its associated complications and pathophysiological conditions in humans, including Covid19.

BACKGROUND

All living organisms have some sort of immune system to fight pathogenic microorganisms. Humans have multiple defenses against pathogenic microorganisms including bacteria, viruses, and fungi. However, the natural defenses are not always adequate, and the patient requires external support to combat the infection. For example, the white blood cells called lymphocytes of the immune system defend against viral infections. However, in the case of novel viruses, the defensive lymphocytes are initially low in number and it may take days to proliferate to effective numbers that can fight the infection. Moreover, the human defense system may fail against both the known and new types of infection. Thus, external support to combat the infections become essential. The external support can be one that directly kills or prevent the growth of microorganism, such as antibiotics. Or the external support can be supportive, for example, ventilation, hydration, and nourishing the body.

With the increasing occurrences of new forms of pathogens and increasing resistance against the known, a need is always there for more effective means to counter the infections.

SUMMARY OF THE INVENTION

The principal object of the present invention is to cure the viral infection at all stage of infection.

It is another object of the present invention to reduce complications associated with viral infection.

It is still another object of the present invention to prevent the replication of the viruses in the human body.

It is yet another object of the present invention to improve oxygen uptake by the lungs.

In one aspect, disclosed is a method of treating viral infections in humans. The method comprising administering to a patient a composition of dextrose and ethanol. The composition can be administered in the form of an infusion.

In one aspect, the method comprises administrating a 5%-10% alcohol in 5% dextrose sterile, nonpyrogenic, hypertonic solution and special cool inhaler alcohol with Methylene blue.

In one aspect, disclosed is a method to enhance oxygen uptake in a patient on a ventilator. The method includes the steps of administering to a patient through the respiratory route oxygen having helium gas in a predetermined range.

In one case, the oxygen includes the excited oxygen atoms that are absorbed to a greater extent compared to normal oxygen. The oxygen can be bubbled through a solution of methylene blue in water, wherein the solution is irradiated by intense pulsating light of a predetermined wavelength for obtaining the excited oxygen atoms.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The accompanying figures, which are incorporated herein, form part of the specification and illustrate embodiments of the present invention. Together with the description, the figures further explain the principles of the present invention and to enable a person skilled in the relevant arts to make and use the invention.

DETAILED DESCRIPTION

Figure 1:
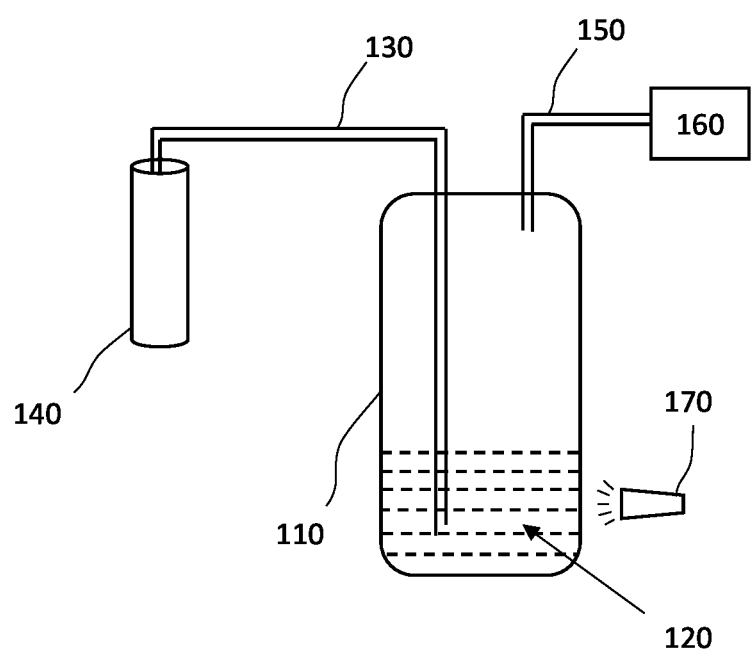
FIG. 1 is a block diagram, showing an examplary embodiment of the present invention.

Subject matter will now be described more fully hereinafter. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, the reasonably broad scope for claimed or covered subject matter is intended. Among other things, for example, the subject matter may be embodied as apparatus and methods of use thereof. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention since the scope of the invention will be best defined by the allowed claims of any resulting patent.

The following detailed description is described with reference to the drawings, wherein like reference numerals are used to refer to like elements throughout. In the following description, for purposes of explanation, specific details may be set forth in order to provide a thorough understanding of the subject innovation. It may be evident, however, that the claimed subject matter may be practiced without these specific details. In other instances, well-known structures and apparatus are shown in block diagram form in order to facilitate describing the subject innovation. Moreover, the drawings may not be to scale.

Disclosed is a method of treating viral infection and its associated complications and pathophysiological conditions. Particularly, the disclosed is a method for treating a patient infected by SARS viruses. Particularly, disclosed in a method of treating a viral infection caused by COVID-19 viruses. The disclosed method provides relief at the early stages of the infections and prevents the progress of the infection by preventing the replication of the viruses in the human body. Moreover, the disclosed method provided for improved oxygen uptake in patients having adverse breathing complications due to the viral infection.

Covid-19 discovered in 2019 is named severe acute respiratory syndrome coronavirus-2 (SARS-CoV-2, 2019-nCoV) has high homology to SARS-COV, which cause acute respiratory distress syndrome (ARDS). The lungs are primarily affected by a SARS infection, and responsible for high mortality. Covid-19 directly impacts the lungs and damages the wall and the lining of the alveoli. The alveoli are responsible for transferring oxygen to the blood vessels. The inflamed alveoli have reduced capability to transfer the oxygen and thus resulting in oxygen deficiency and the hypoxia sets in.

The disclosed method provides for enhancing the oxygen uptake by the lungs and nourishing the patient. The disclosed method provides for the cure of viral infection such as Tuberculosis at the early stages. The method aims to prevent the progress of viral infection by inhibiting viral replication in the human body. The method further provides for reducing the viral load in the human body.

In one exemplary embodiment, the method includes a step of intravenously administering a solution of ethanol in dextrose injection solution. In one case, the patient can be administered 5% ethanol in a 5% dextrose sterile solution for parenteral administration. The injectable solutions "ALCOHOL 5% AND DEXTROSE 5%" and "ALCOHOL 10% AND DEXTROSE 5%" were approved by FDA for increased caloric intake. The solution has also been used for alcohol poisoning and controlling acute alcohol withdrawal symptoms. The inventors of the disclosed method surprisingly discovered that the above injection solution decreases the viral load in the human body and prevents the replication of the viruses. Additionally, the alcohol in dextrose injection solution has sedative effects that reduce the need for sedatives. However, it may be advisable to keep the administration rate such that the exhaled percentage of the alcohol is 0.6% or less.

For the patients suffering from viral infections and additionally having respiratory complications, the disclosed method provides for administering about 0.1 to 4% helium gas to reduce the resistance for oxygen uptake and enhances oxygen transfer by alveoli. The oxygen transfer can be further improved by administering to the patient excited oxygen atoms. In one exemplary embodiment, the oxygen can be bubbled through a solution of methylene blue in the water while irradiating the solution with intense pulsating light waves. The normal ground state of atomic oxygen has two unpaired electrons. The disclosed method excites one of the two electrons, wherein the centrifugal overbalances the centripetal forces. These excited oxygen molecules show enhanced oxygen transfer through the alveoli membrane. Additionally, the diuretics and Positive end-expiratory pressure (PPEP) therapy can also be administered for improving the oxygenation of the entire body. The excited oxygen atoms were also found to have microbiocidal action and viricidal action.

In one embodiment, the method further comprises a step of bringing the pH of the human body around 5.5 for a predetermined duration of time.

The disclosed method is effective in curing pathogenic infections including the bacterial, viral, and fungal.

In one embodiment, disclosed is a device for producing excited oxygen atoms that has a better penetration in the lungs. The excited oxygen atoms are absorbed more by the lungs in comparison to a normal oxygen atom. Referring to FIG. 1, the disclosed device comprises an enclosed cylindrical container 110. The container 110 having a solution 120 of methylene blue in water up to a predetermined height. An inlet 130 is dipped in the solution, wherein the inlet is in fluid communication with a fluid cylinder 140. The container 110 having an outlet 150 near its top, wherein the outlet can be connected to a patient respiration system 160. The device further comprises an irradiation source 170 that can produce intense light pulses of a wavelength between 600-700 nanometers in a circular pattern and 750-950 nanometers in a continuous pattern.

Figure 2:
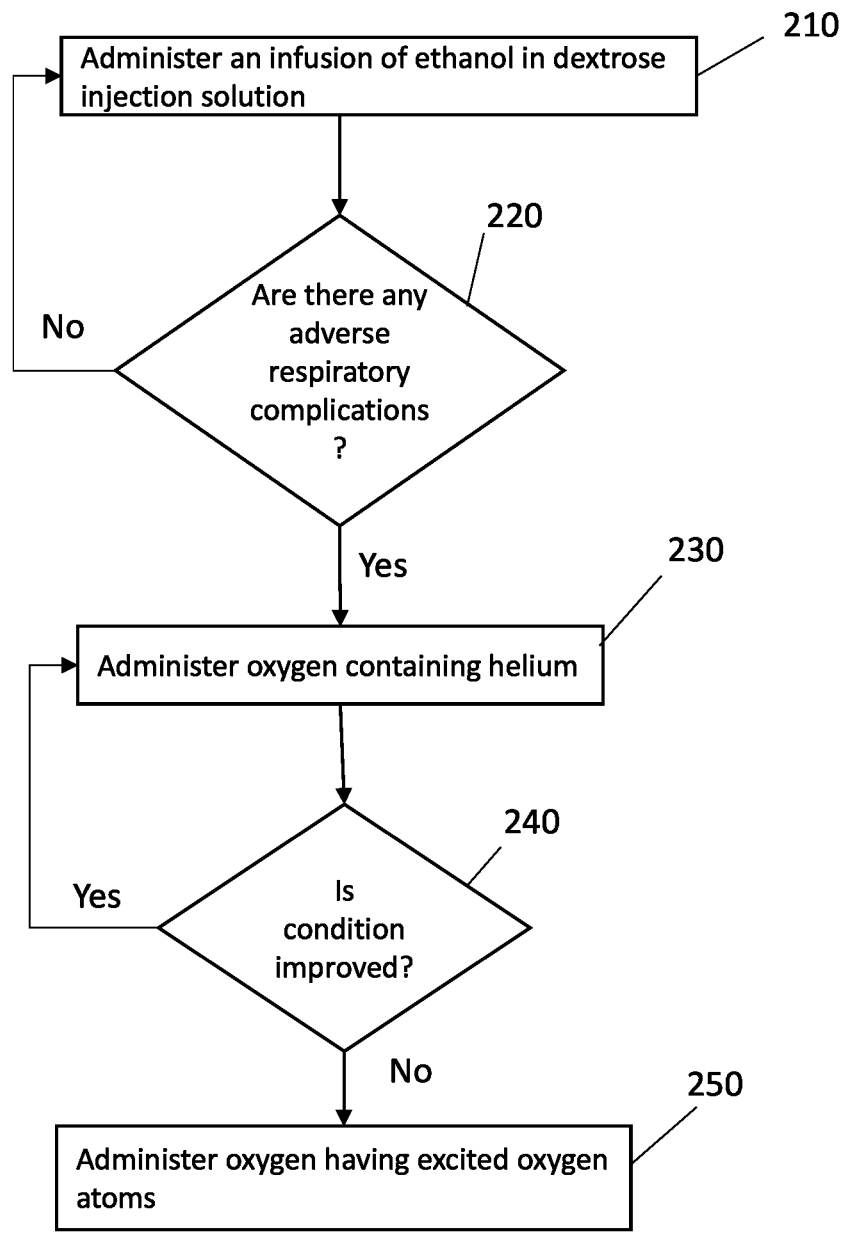
FIG. 2 is a flow chart showing an examplary embodiment of the present invention.

Referring to FIG. 2, which is a flowchart showing an embodiment of the disclosed method for treating infections in humans and its associated complications. The disclosed method provides for curing the infection caused by bacteria, fungi, viruses, other known pathogens in humans. The method includes the step of administering an infusion of ethanol in dextrose injection solution to a patient suffering from an infection, at step 210. In case, a patient is having adverse respiratory complications making breathing difficult, a check for adverse respiratory complications can be made at step 220. If the patient is having adverse respiratory complications, the patient on the ventilator or other respiration support system can be administered oxygen-containing helium, at step 230. The helium reduces the oxygen resistance of the lungs. If the respiratory condition of the patient improves, the process can be continued for a predetermined duration. If the respiratory condition does not improve, the patient can be administered oxygen having the excited oxygen atoms, at step 250.

What is claimed is:

1. A method of enhancing oxygen uptake by lungs, the method comprises:
    bubbling oxygen through a solution, the solution comprising methylene blue in water, wherein the solution is irradiated by intense light pulses, obtaining excited oxygen atoms; and
    administering air comprising the excited oxygen atoms to a patient.

2. The method according to claim 1, wherein the intense light pulses are of wavelength 600-700 nanometers in a circular pattern and 750-950 nanometers in a continuous pattern.

3. The method according to claim 1, wherein the air further comprising helium in a concentration of about 0.5-4%.

4. A device for producing excited oxygen atoms, the device comprising:
    an enclosed container having a solution of methylene blue in water;

an inlet dipped in the solution, the inlet in fluid communication with a compressed gas source;
an outlet configured near a top of the container, the outlet fluidly connecting an interior of the enclosed container with a patient respiration support device; and
a source of light pulses configured to irradiate the solution.

5. The device according to claim 4, wherein the compressed gas source comprises oxygen gas.

6. The device according to claim 5, wherein the light pulses are of wavelength 600-700 nanometers in a circular pattern and 750-950 nanometers in a continuous pattern.

* * * * *